United States Patent
Saltykov et al.

(10) Patent No.: US 8,229,151 B2
(45) Date of Patent: Jul. 24, 2012

(54) COMPLETELY-IN-CANAL HEARING INSTRUMENT WITH ROBUST FEEDBACK STABILITY

(75) Inventors: Oleg Saltykov, Fairlawn, NJ (US); Fred McBagonluri, East Windsor, NJ (US)

(73) Assignee: Siemens Hearing Instruments Inc., Piscataway, NJ (US)

( * ) Notice: Subject to any disclaimer, the term of this patent is extended or adjusted under 35 U.S.C. 154(b) by 1224 days.

(21) Appl. No.: 11/846,112

(22) Filed: Aug. 28, 2007

(65) Prior Publication Data

US 2009/0060241 A1   Mar. 5, 2009

(51) Int. Cl.
 *H04R 25/00* (2006.01)
(52) U.S. Cl. .................................................. 381/328
(58) Field of Classification Search .................. 381/328
 See application file for complete search history.

(56) References Cited

U.S. PATENT DOCUMENTS

| 2,634,337 | A | * | 4/1953 | Bland | 381/322 |
| 5,357,576 | A |   | 10/1994 | Arndt | |
| 5,875,254 | A | * | 2/1999 | Hanright | 381/329 |
| 6,078,677 | A |   | 6/2000 | Dolleman | |
| 6,459,800 | B1 | * | 10/2002 | Brimhall | 381/324 |
| 2005/0074138 | A1 |   | 4/2005 | Saltykov | |
| 2006/0050912 | A1 |   | 3/2006 | Kidd et al. | |
| 2008/0212804 | A1 | * | 9/2008 | Watanabe | 381/120 |

FOREIGN PATENT DOCUMENTS

WO   00/47016 A   8/2000

OTHER PUBLICATIONS

Waller, "Vibrations of Free Elliptical Plates", Proceedings of the Physical Society of London, Institute of Physics Publishing, Bristol, GB, vol. B63, No. 6, Jun. 1, 1950, pp. 451-455.
International Search Report including Notification of Transmittal of the International Search Report, International Search Report, and Written Opinion of the International Searching Authority.

* cited by examiner

*Primary Examiner* — Jianchun Qin
(74) *Attorney, Agent, or Firm* — Francis G Montgomery

(57) ABSTRACT

A CIC hearing instrument and appertaining method are provided that improve feedback stability. Accordingly, the microphone inlet is located on the faceplate of the instrument at a position of least vibration. Furthermore, the receiver is located in the device such that its vibrating membrane is parallel to a plane calculated to include a line of minimal vibration on the faceplate and a center of gravity for the instrument.

2 Claims, 7 Drawing Sheets

COMPLETELY-IN-CANAL HEARING INSTRUMENT WITH ROBUST FEEDBACK STABILITY

BACKGROUND

The present invention is directed to a completely-in-canal (CIC) hearing aid constructed to have a robust feedback stability.

A typical CIC instrument can operate normally when its acoustic gain does not exceed 40 dB. If the acoustic gain of a CIC instrument gets increased, the frequency response of the instrument develops sharp peaks. After the gain of a CIC instrument exceeds a certain threshold, the instrument becomes unstable and begins to oscillate at a frequency of the highest peak of the frequency response. A typical CIC instrument comprises a shell, a faceplate, a battery, a hybrid, a microphone, and a receiver.

The purpose of the receiver is to convert the electrical signals into an acoustic sound pressure. As a by-product of its operation, a receiver creates mechanical vibrations. A typical CIC receiver is shown on FIG. 1. Its construction is described in related art publications (e.g., U.S. Pat. No. 6,078,677), in which its FIG. 2 (corresponding to FIG. 1 in the present application), shows a longitudinal section of an electroacoustic transducer 1.100, wherein an actuator comprises an electric coil 1.31 which is connected via an electric line 1.32 extending through the lower case 1.4 to terminals 1.33 mounted on the outer surface of the housing 1.2. Placed within a magnet housing 1.34 is a magnetic member 1.35. An air gap 1.36 of the magnetic member 1.35 is aligned with an air gap 1.37 of the coil 1.31. A U-shaped armature 1.40 has a first leg 1.41 attached to the magnet housing 1.34 and a second leg 1.42 extending into the aligned air gaps 1.36 and 1.37. Attached to the end of the second leg 1.42 is the fork 1.21.

If an externally generated current is presented to the coil 1.31, a force is exerted on the armature 1.40 by the magnetic field generated by the magnetic member 1.35. As a result thereof, a displacement is generated in the longitudinal direction of the fork, thereby moving the diaphragm to generate a pressure wave. The cover 1.3 has an opening 1.46 through which the interior of the housing 1.2 between the cover 1.3 and the diaphragm 1.10 communicates with the outside world. Attached to the housing is a substantially cylindrical nozzle 1.47 to which, if desired, a flexible tube can be fastened for guiding pressure waves.

This figure shows that the diaphragm 1.10 may have a layered structure. More in particular, the diaphragm 1.10 comprises a thin flexible foil 1.51 and a reinforcement layer 1.52 attached thereto, e.g. by gluing. The reinforcement layer 1.52 has a thickness exceeding that of the foil 1.51 and has a surface defining the central diaphragm portion 1.11. The part of the foil 1.51 projecting beyond the reinforcement layer 1.52 defines the edge portion 1.12.

A simplified vibration model of a CIC receiver is shown in FIG. 2 of the present application. It comprises a case 20, a U-shaped armature 30 and a membrane 40. The motor (not shown for simplicity of illustration) creates various forces 50 that cause the membrane 40 to vibrate: the force applied to the U-shaped armature 30 and the reaction force applied to the case 20. The major reason for an unstable operation of a CIC instrument is the receiver vibrations that cause the CIC faceplate to radiate the sound pressure into the microphone.

Therefore the receiver has to be isolated from direct contact with the shell or other CIC components inside a CIC instrument. As FIGS. 3 and 4 illustrate, the receiver 100 of a typical CIC instrument is placed inside the CIC shell 12 and attached to the shell tip 14 with a flexible tube 66. The tube 66 feeds the sound pressure, generated by the receiver 100, into the ear of the user. The tube 66 also isolates the vibrations that the receiver 100 creates, from spreading into the CIC instrument. A receiver in a conventional CIC instrument also has a soft boot or studs 60 that prevents the receiver walls from forming a direct contact with CIC elements inside the shell 12. When such a direct contact occurs, the CIC becomes unstable or its frequency response begins to comprise many sharp and undesirable peaks.

A conventional CIC instrument performance is not consistent. Even if the same assembly worker builds two "identical" instruments, their performance would be quite different because the position of a receiver inside the shell is not fixed. The receiver can be moved and turned before it is fixed to its final position, and the worker can not replicate such a position even if the shell of the second instrument is exactly the same as that of the first instrument.

A construction of a receiver and a hearing instrument is described in the related art U.S. Patent Publication No. 2005/0074138; this reference teaches how to build instruments with a higher consistency of performance. In the instrument disclosed, the virtual receiver position is chosen by using custom 3-D software before the shell is manufactured. Then, the real shell is produced by a stereo lithographic apparatus (SLA) process with all necessary features that will support the receiver in a designated place. The construction of the receiver and the supporting structures guarantee that the CIC instrument will operate without the feedback with the acoustic gain up to 40 dB.

A typical construction of a CIC instrument 10 with an RSA receiver 100 is shown in FIG. 5, that comprises a faceplate 11, shell 12, microphone 13, battery door 15 with battery 16, hybrid 17, and vent 18. Such an instrument has a maximum gain limitation of 40 dB. However, a CIC instrument with an RSA receiver can be built with higher maximum stable gain by following special rules during its virtual assembly.

SUMMARY

The present invention provides a superior construction of a CIC instrument with at least 10 dB higher feedback threshold than typical conventional CIC instruments. Accordingly, a CIC hearing instrument is provided, comprising: a shell; a microphone internal to the shell; a receiver that is suspended inside of the shell, the receiver having a membrane; and a faceplate having a microphone inlet hole whose center is located along a line of minimal vibrational sound pressure on the faceplate.

Additionally, a method is provided for producing a CIC hearing instrument, comprising: providing a receiver and microphone within a hearing aid shell and a faceplate on top of the shell; determining a line of minimal vibrational sound pressure on the faceplate; and producing a microphone inlet hole within the faceplate, the hole having a center located along the line of minimal vibrational sound pressure.

According to an embodiment, the receiver is arranged within the shell by first calculating a plane that passes through a line of minimal vibration on the shell and a calculated center of mass of the device. Then the receiver is placed so that its membrane is parallel to this calculated plane

DESCRIPTION OF THE DRAWINGS

The invention is explained with respect to various preferred embodiments illustrated in the following drawings and described below.

DETAILED DESCRIPTION OF THE PREFERRED EMBODIMENTS

Figure 1:
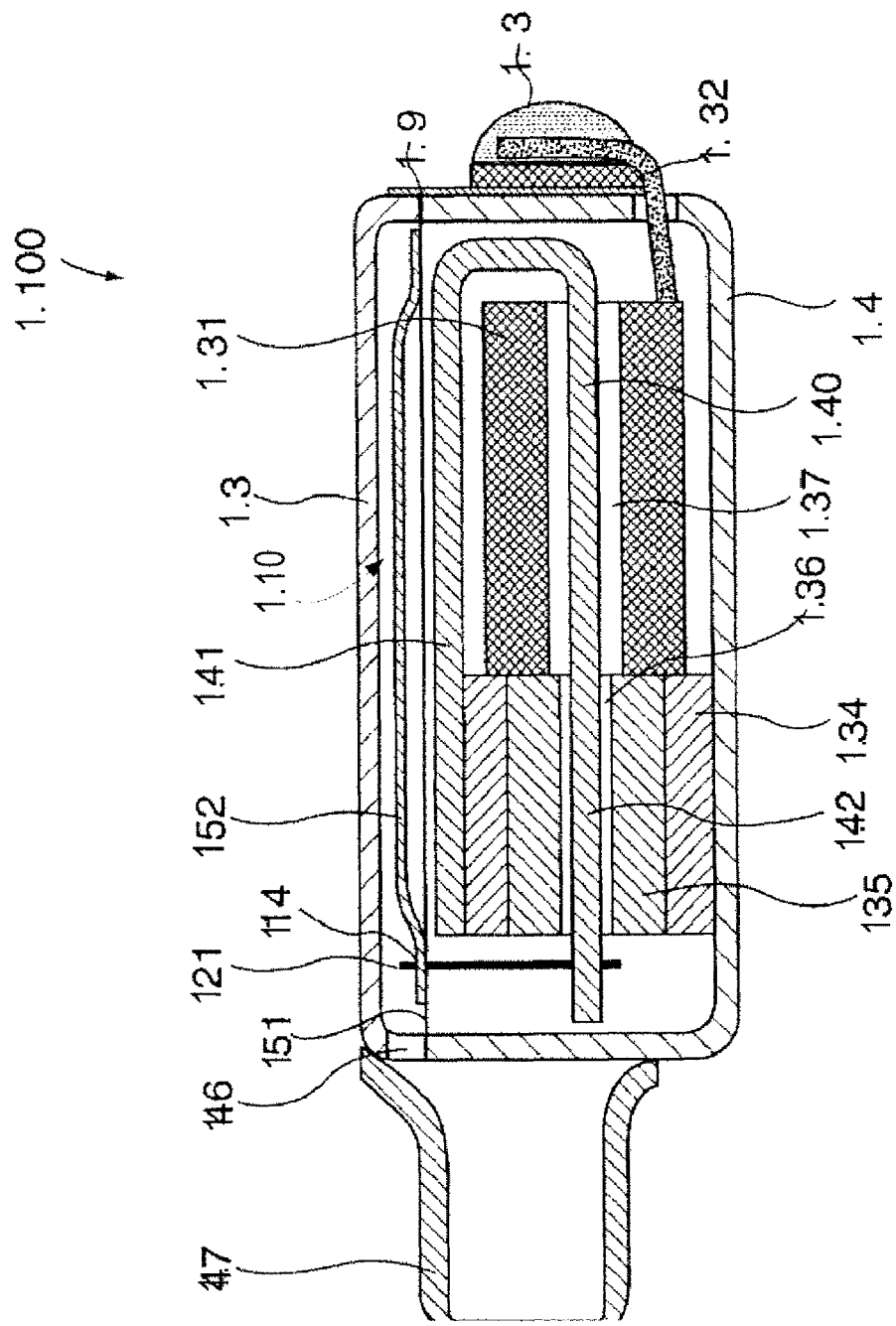
FIG. 1 is a pictorial illustration of a known CIC receiver.
Figure 2:
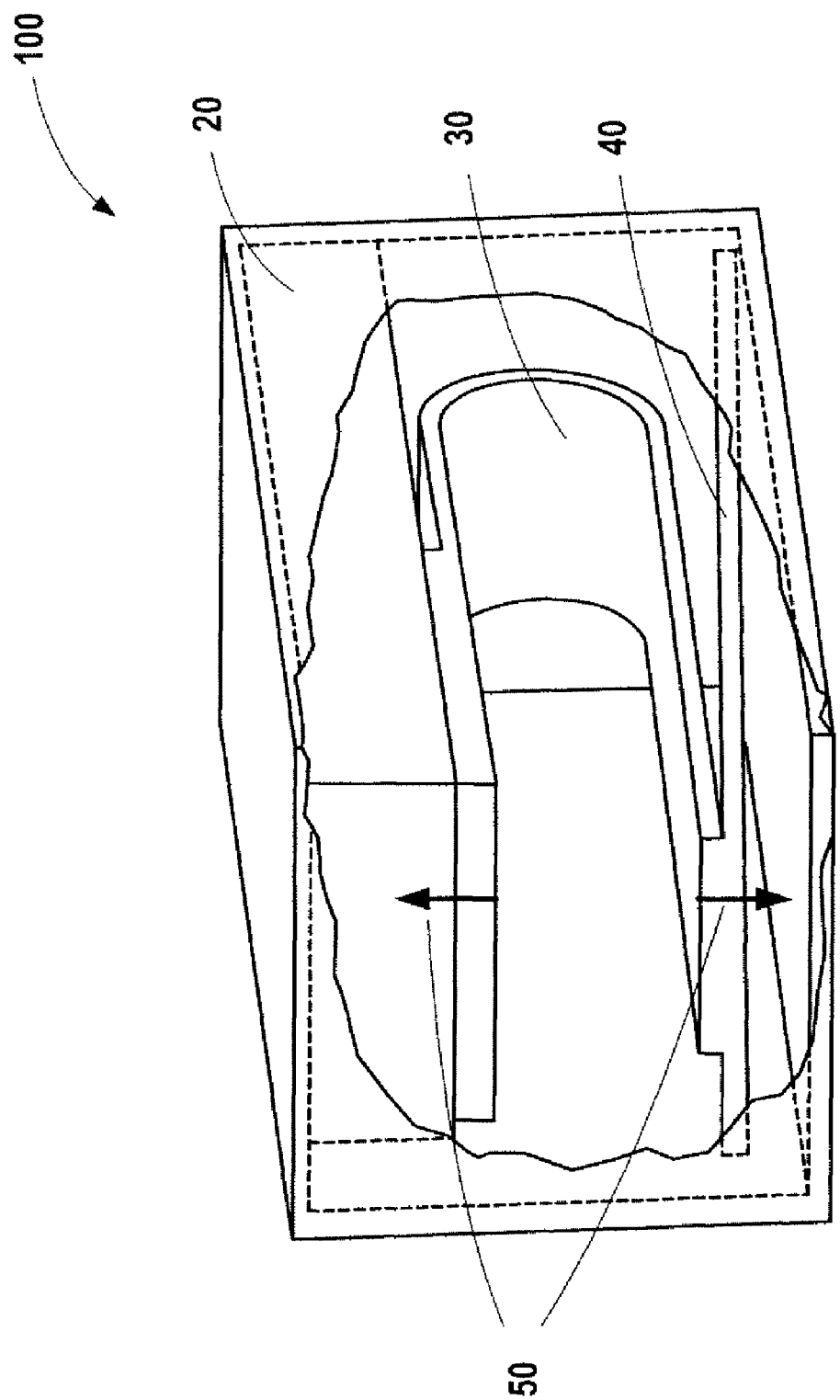
FIG. 2 is a pictorial illustration of a simple vibrational model of a CIC receiver.
Figure 3:
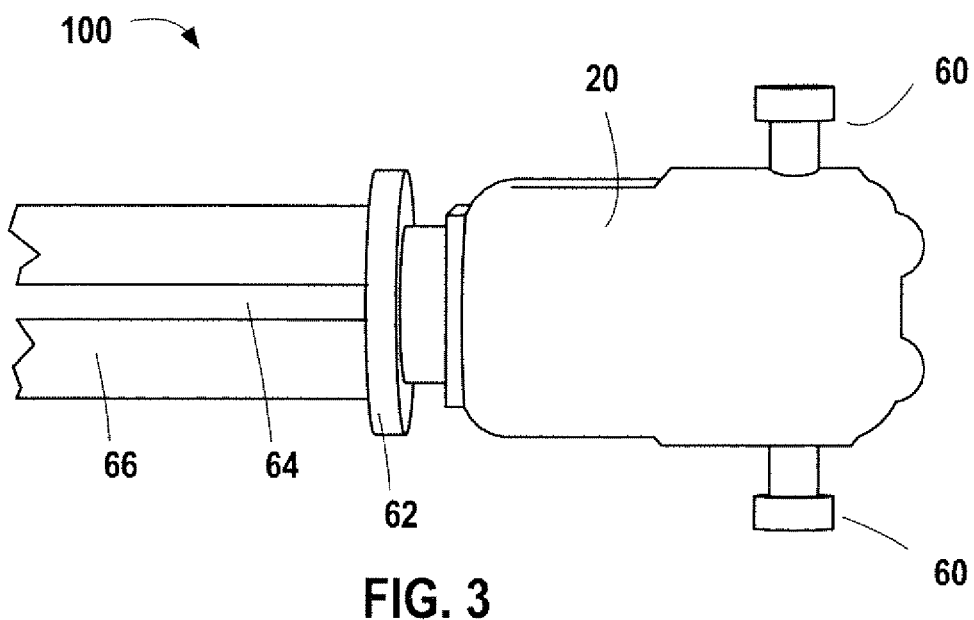
FIG. 3 is a pictorial illustration of a known CIC receiver with suspension elements.
Figure 4:
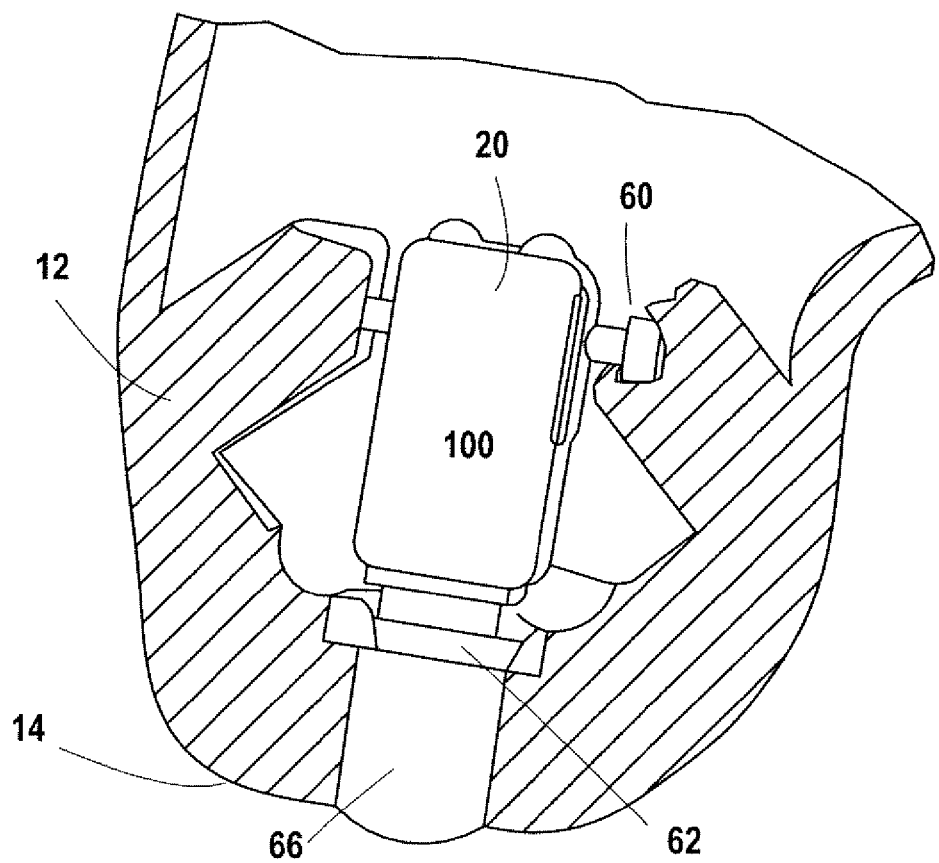
FIG. 4 is a pictorial illustration of a CIC receiver suspended inside of a CIC shell.
Figure 5:
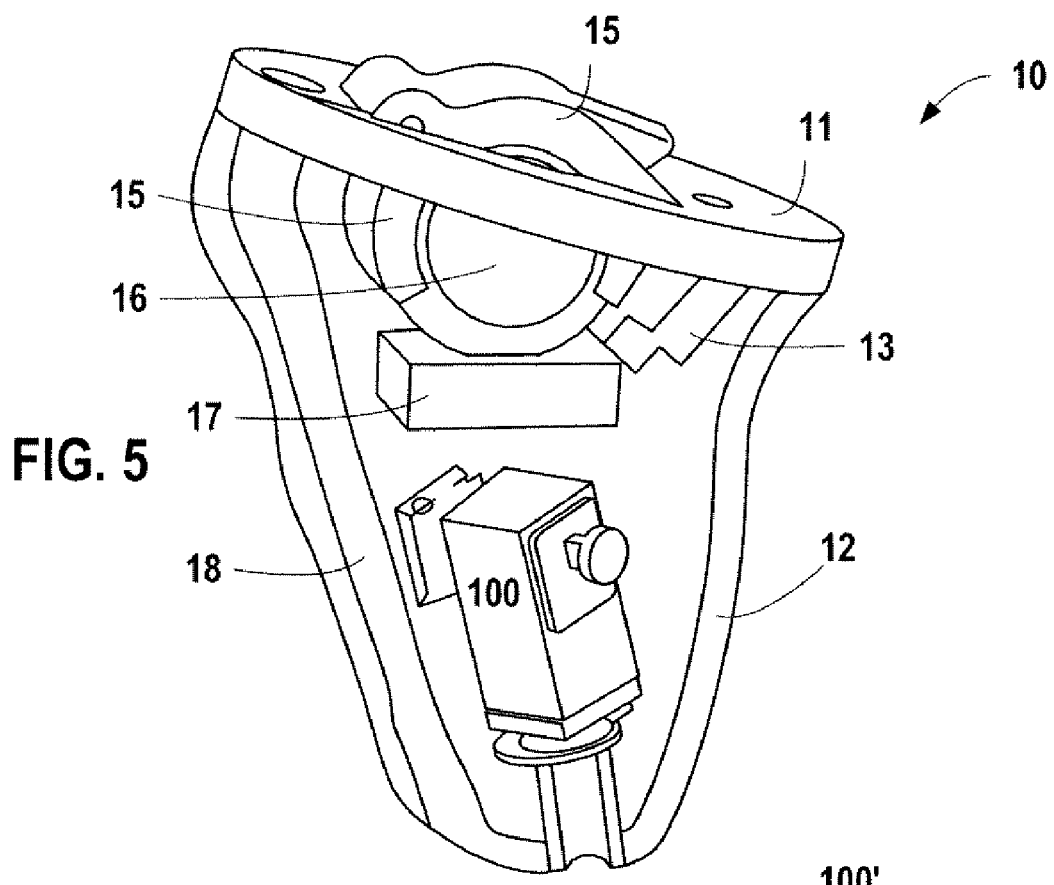
FIG. 5 is a pictorial illustration of a construction of a CIC instrument.
Figure 6:
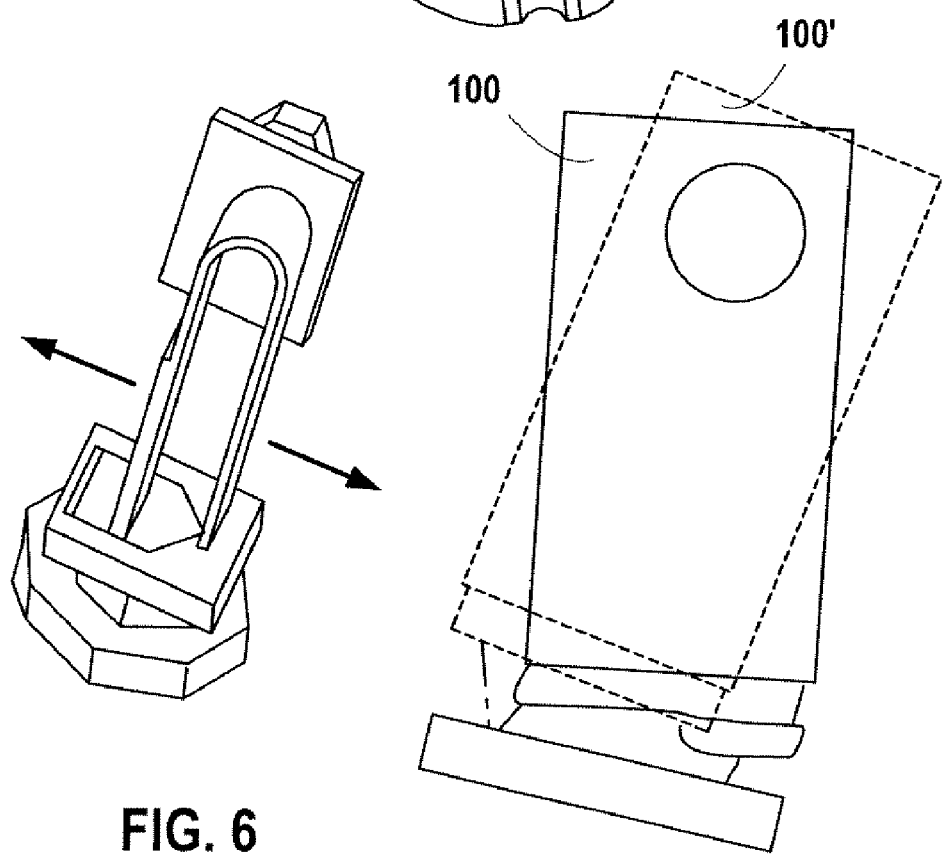
FIG. 6 is a pictorial illustration of a typical receiver vibration pattern caused by reaction forces of the receiver moving elements.
Figure 7:
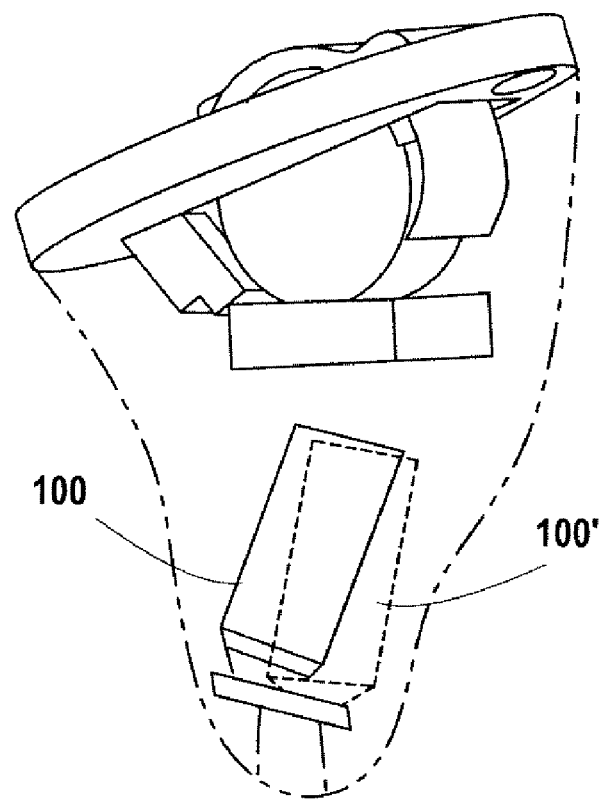
FIG. 7 is a further pictorial illustration of a typical receiver vibration pattern caused by reaction forces of the receiver moving elements.
Figure 8:
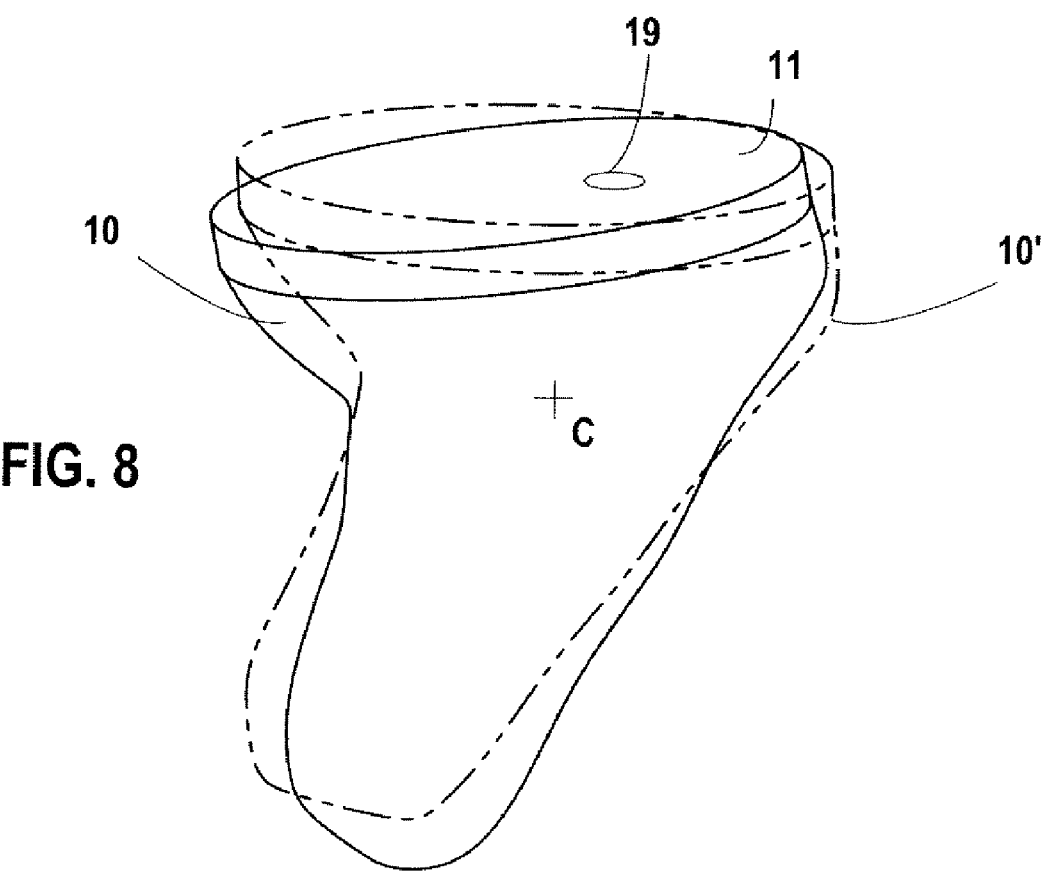
FIG. 8 is a pictorial illustration of a typical vibration pattern of a CIC instrument caused by reaction forces of the receiver moving elements.

FIGS. 6 and 7 show a typical pattern of RSA receiver vibrations, which is caused by the vibrating U-shaped armature and a membrane. In these figures, the receiver 100 vibrates between a first 100 and second 100' position. The vibrating receiver 100 causes the whole CIC instrument 10 to vibrate between a first 10 and second 10' position, as is illustrated in FIG. 8. A typical CIC instrument will vibrate about its center of mass C. Putting such an instrument into the user's ear will affect the vibration pattern, but not a great deal, since the ear tissues are soft.

Figure 9:
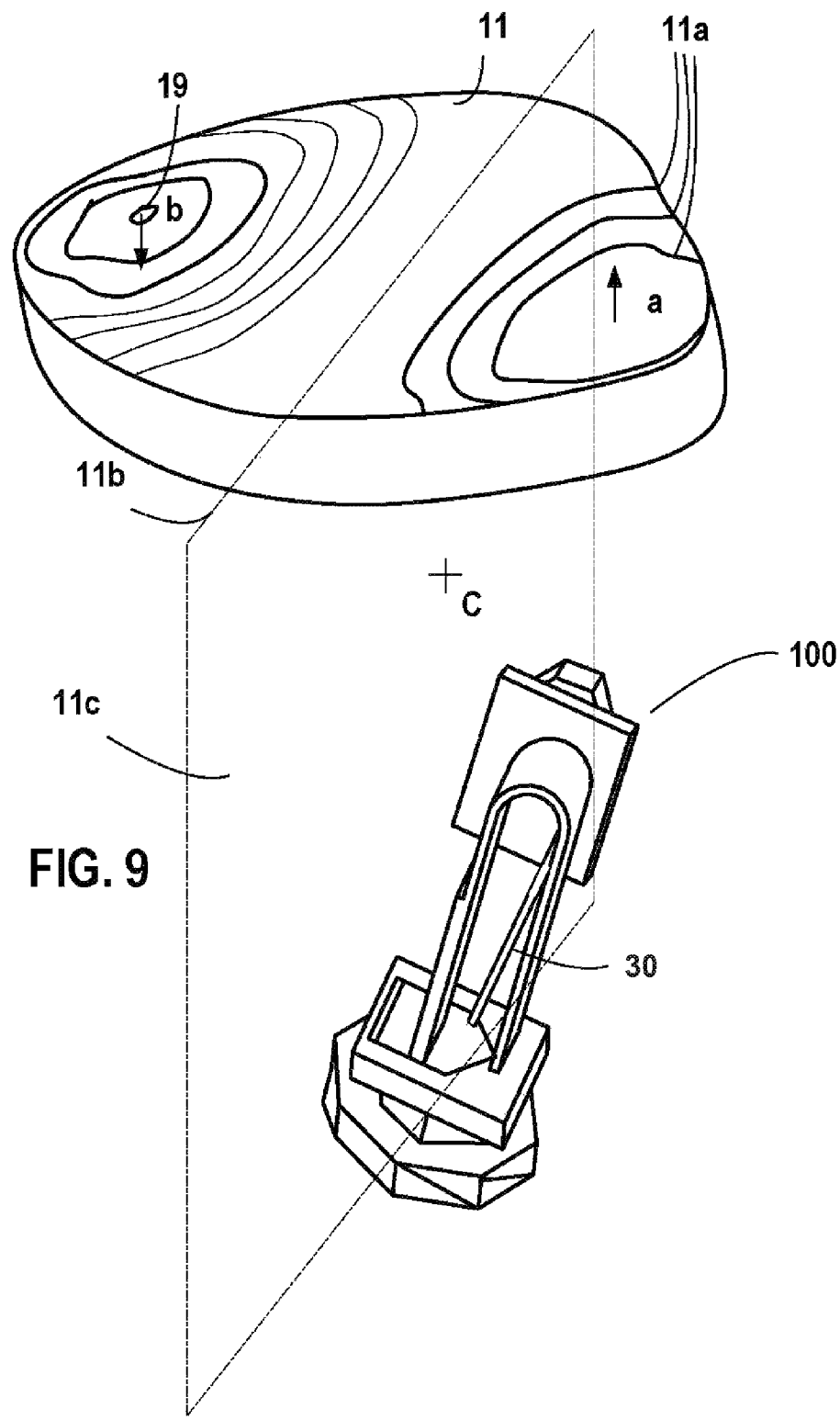
FIG. 9 is a pictorial illustration of a typical distribution of a sound pressure, generated on a surface of a CIC faceplate, caused by the instrument vibrations.

The vibration of a CIC instrument 10 will cause the faceplate 11 to vibrate as well. The faceplate 11 has a microphone inlet 19 which picks up the sound pressure and feeds it into the microphone 13. In addition to a useful sound pressure (speech, music, etc), the microphone 13 will pick-up the vibrational sound pressure that the faceplate 11 creates due to its own mechanical vibrations. A possible distribution of a vibrational sound pressure on the faceplate 11 is shown in FIG. 9, which indicates two areas of maximum vibrational sound pressure—for positive normal displacements and for negative normal displacements. Also lines of equal sound pressure 11a are shown: the sound pressure will be the highest at the centers of the areas. The line of a minimal vibrational sound pressure divides the areas of maximum sound pressure for positive and negative normal displacements.

Figure 10:
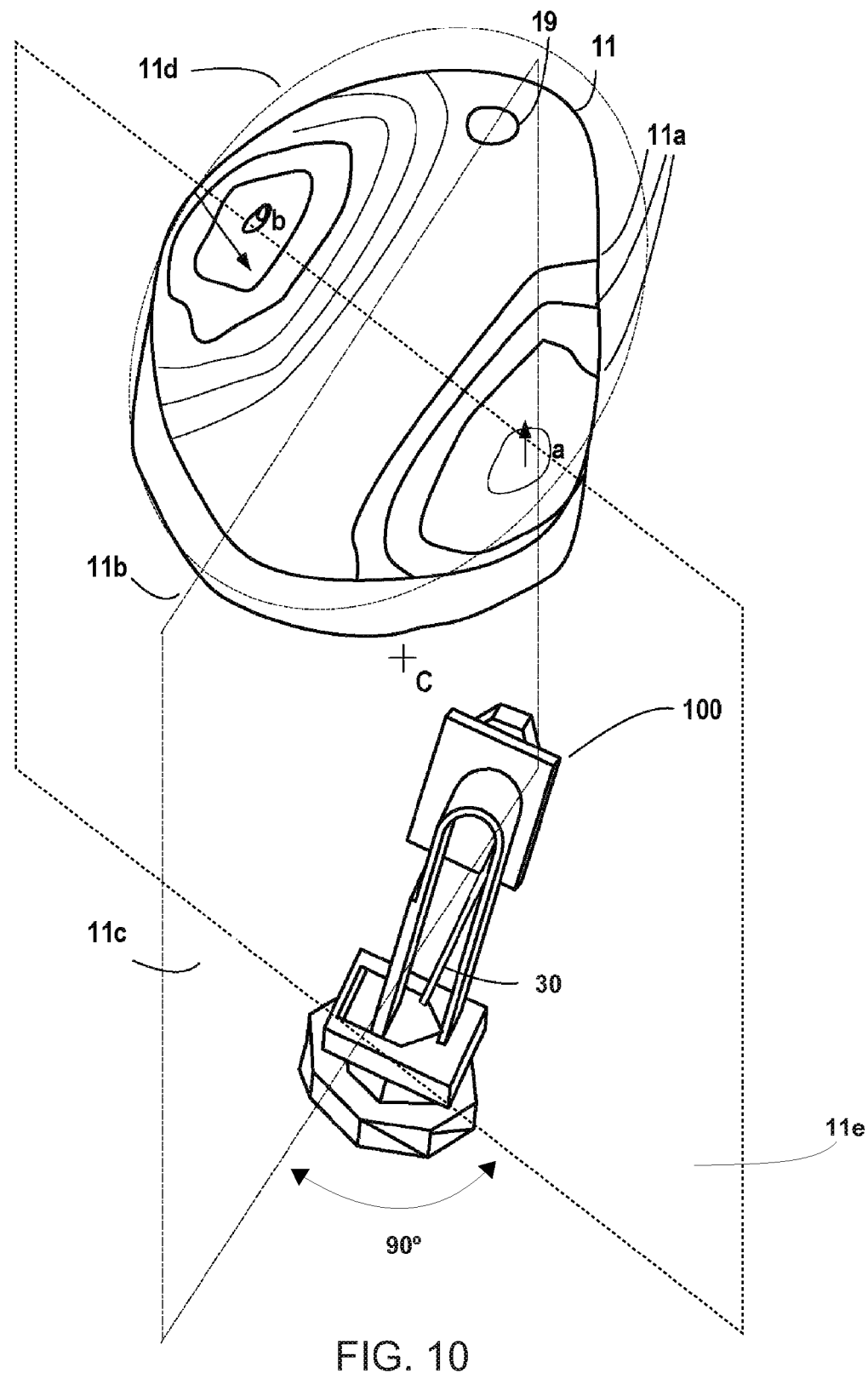
FIG. 10 is a pictorial illustration of a preferred receiver orientation that minimizes the vibration-related sound pressure near the microphone inlet.

If the microphone inlet 19 is positioned close to the center of areas of maximum vibrational sound pressure, the feedback performance of a CIC instrument would be the worst, as is illustrated by FIG. 9. As shown in this figure, the faceplate 11 comprises lines of equal vibrational sound pressure 11a, different halves of the faceplate 11 are vibrating 180° out of phase with each other, where an area a has a maximum vibrational sound pressure for positive normal displacement, and area b has a maximum sound pressure for negative normal displacement. As can be seen, in this worst placement configuration, the microphone inlet 19 is located at precisely the area b at which the vibrational sound pressure is the greatest. An axis 11b is defined which is a line of minimal vibration sound pressure. Although it is illustrated in FIGS. 9 and 10 as a straight line, it could, in fact, be a curved line, depending on the particular geometry and materials used (e.g., if flexible). In the preferred embodiment, the faceplate is rigid and thus the axis 11b is generally straight. A straight line can be calculated from the curved line, if need be.

FIG. 10 illustrates the placement of the microphone inlet 19 on the axis of minimal vibration 11b, creating a substantial improvement in the feedback stability of a CIC instrument. The placement of the microphone inlet 19 on the generally-planar faceplate 11 is determined as follows. The faceplate 11 is represented as an ellipse 11d approximating the oval shape of the faceplate 11, and its major axis 11b is calculated. The center of gravity C of the hearing instrument is then determined, and a plane of minimal vibration 11c is calculated that includes the major axis 11b of the ellipse as well as the calculated center of gravity C. A receiver plane of vibration 11e contains the plane in which the U-shaped armature 30 vibrates and moves, and is normal with respect to the plane of minimal vibration 11c. Once the center of gravity C and the plane 11c is calculated, the receiver 100 can be positioned so that its generally planar membrane or diaphragm 40 is parallel to the plane 11c. This helps to minimize the vibrational effect at the microphone inlet 19. It is also possible to perform the calculation of the center of gravity C in an iterative manner in the situation where the receiver is included in the center of gravity calculations.

The above-described conditions produce an optimal balance for feedback performance, and although modifications can be made, it will generally result in tradeoffs in device performance. Although theoretically the above analysis could be applied one time to an entire family based on a design, variations in CIC instruments are significant enough so that, ideally, the analysis is performed for each instrument. It could be possible to classify CIC instruments into various groups by shape, and then to specify a typical position for the receiver and microphone inlet. The resultant improvements can improve the feedback effects by up to 10 dB.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware components configured to perform the specified functions. The particular implementations shown and described herein are illustrative examples of the invention and are not intended to otherwise limit the scope of the invention in any way. For the sake of brevity, conventional structural and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

TABLE OF REFERENCE CHARACTERS 1.xx related art patent reference characters
10 CIC hearing aid/instrument
11 faceplate
11a lines of equal vibrational sound pressure
12 CIC shell
13 microphone
14 CIC shell tip
15 battery door
16 battery
17 hybrid
18 vent
19 microphone inlet
20 case
30 u-shaped armature
40 membrane
50 motor forces
60 stud
62 stopper ring
64 spline
66 tube
100 receiver

What is claimed is:

1. A hearing instrument for insertion into the ear canal of a user, comprising
 a center of gravity of the hearing instrument;
 a shell, the shell comprising an interior;
 a generally-planar faceplate attached to the shell and comprising an approximately elliptical shape comprising major and minor axes;
 a plane of minimal vibration of the hearing instrument comprising the major axis of the faceplate and the center of gravity of the hearing instrument;
 a receiver positioned in the interior of the shell, the receiver comprising a vibrating armature and a generally-planar diaphragm responsive to the armature, the diaphragm lying in a plane
  normal to a plane defined by the motion of the vibrating armature, where the plane defined by the motion of the vibrating armature intersects the faceplate; and
  parallel to the plane of minimal vibration;
 a microphone positioned in the interior of the shell; and
 a microphone inlet for the microphone located on the major axis.

2. A method for positioning a microphone inlet on the faceplate of a hearing instrument for insertion into the ear canal of a user, the hearing instrument comprising
 a shell, the shell comprising an interior;
 a generally-planar faceplate attached to the shell and comprising an approximately elliptical shape comprising major and minor axes;
 a receiver positioned in the interior of the shell, the receiver comprising a vibrating armature and a generally-planar diaphragm responsive to the armature and lying in a plane normal to a plane defined by the motion of the vibrating armature, where the plane defined by the motion of the vibrating armature intersects the faceplate; and
 a microphone positioned in the interior of the shell,
the method comprising:
 determining the location of the center of gravity of the hearing instrument;
 establishing a plane of minimal vibration of the hearing instrument comprising the major axis of the faceplate and the center of gravity;
 orienting the receiver such that the plane of the diaphragm is parallel to the plane of minimal vibration; and
 placing a microphone inlet for the microphone on the major axis.

* * * * *